United States Patent [19]

Kozloff et al.

[11] 4,375,734

[45] Mar. 8, 1983

[54] PROTECTION OF PLANTS AGAINST FROST INJURY USING ICE NUCLEATION-INHIBITING SPECIES-SPECIFIC BACTERIOPHAGES

[75] Inventors: Lloyd M. Kozloff, San Francisco, Calif.; Russell C. Schnell, Boulder, Colo.

[73] Assignee: University Patents, Inc., Norwalk, Conn.

[21] Appl. No.: 293,643

[22] Filed: Aug. 17, 1981

[51] Int. Cl.³ ............................................. A01G 1/00
[52] U.S. Cl. ............................................. 47/2; 424/93
[58] Field of Search ........................... 47/2, 58; 424/93

[56] References Cited

U.S. PATENT DOCUMENTS 4,045,910  9/1977  Arny et al. ................................. 47/2
4,161,084  7/1979  Arny et al. ................................. 47/2

OTHER PUBLICATIONS

Biological Control of Plant Pathogens, Baker & Cook, 1974, W. H. Freeman & Co., p. 42.
Plant Cold Hardiness and Freezing Stress, Li & Sakai, 1978, Academic Presa pp. 249-263.
Some Properties of Erwinia . . . , Ritchie et al, PHYTA, vol. 69 (10) 1979, pp. 1078-1083.

*Primary Examiner*—Robert E. Bagwill
*Attorney, Agent, or Firm*—Jerome M. Teplitz

[57]    ABSTRACT

Frost-sensitive plants are protected against frost injury by topical application thereto of non-phytotoxic virulent bacteriophages which are species-specific to the ice-nucleating bacteria normally present on the plants. The bacteriophages selectively attack the ice-nucleating bacteria and inhibit their ice-nucleating activity, thereby reducing the temperature at which frost injury occurs.

14 Claims, No Drawings

PROTECTION OF PLANTS AGAINST FROST INJURY USING ICE NUCLEATION-INHIBITING SPECIES-SPECIFIC BACTERIOPHAGES

BACKGROUND OF THE INVENTION

The invention described herein was made in the course of work under a grant or award from the Department of Health, Education and Welfare.

This invention relates to the protection of frost-sensitive plants against frost injury and, more particularly, to the inhibition of ice formation in plant tissues at moderate supercooling temperatures.

Damage to crops by frost is one of the leading causes of loss in agricultural output due to natural phenomenon variability in the world, to be exceeded only by drought and flooding, pests and disease. It is estimated that from 5-15% of the gross world agricultural product may be so lost to frost damage in one year. In some regional areas (i.e. counties, valleys) the loss may approach 100%.

The greatest amount of frost damage to sensitive crops does not occur in northern or cold climates. Instead, it occurs at mid- and low-latitudes and at high altitude equatorial locations where high value food crops such as soybean, corn, orchard fruits, and vegetables are grown. For instance, the orchards of California, vineyards of Italy, the corn and soybeans of Iowa, and potatoes of Ecuador all suffer damage each year from the same phenomenon—light night frost at temperatures from $-1°$ C. to $-4°$ C.

It has been estimated by the United States Department of Agriculture that about 1.5 billion dollars of agricultural products is lost to frost damage in the United States each year. The world-wide total is probably in excess of 10 billion dollars.

For the most part, present frost protection methods are centered around the principle of maintaining heat in a crop to keep it from cooling below the freezing point where frost is imminent. This is done by a variety of methods such as burning oil or natural gas, stirring the air over crops, sprinkling the crops with water, and covering them. With the cost of petroleum becoming more expensive and pressures against polluting the air with anthropogenic fires, heating large areas of agricultural land to prevent frost damages may become increasingly unpopular in the future. Also, these measures all require a considerable amount of equipment, trained and available manpower, and are capital intensive.

In addition to these physical methods, chemical methods of frost protection for growing plants have been attempted by application of various chemical compounds onto the plants with the view of lowering the temperature at which the plant tissues would freeze. These previously proposed chemical methods have tended to be unreliable, expensive, and ecologically unsound.

Frost damage to plants occurs when intracellular liquid in the plant tissues freezes with resulting rupture of adjacent cell walls and cell membranes. It is known that plant tissues may supercool to temperatures of around $-6°$ C. in the absence of external ice nuclei. The internal plant tissues do not generally initiate ice at temperatures warmer than this $-6°$ C. threshold.

It has recently been established that there are a very few bacteria species which can act as ice-forming nuclei at relatively warm temperatures, i.e., $-1°$ C. to $-3°$ C. The bacteria *Erwinia herbicola* and *Pseudomonus syringae* have been identified as being representative, if not the sole species, of these bacteria acting as ice nucleants on plant tissues.

To protect plants from frost damage, it is therefore desirable to have available means for reducing the populations or otherwise inhibiting the ice-nucleating activity of the ice-nucleating bacteria on plant leaves, so as to thereby reduce the temperature at which frost injury occurs to temperatures approaching $-6°$ C. The use of various chemical bactericides for this purpose has not thus far proven to be a satisfactory approach, since besides being expensive and ecologically unsound, such bactericides have not been species-specific to the ice-nucleating bacteria, but instead have been deleterious to the plants by also killing the beneficial bacteria.

Another recently proposed approach to this problem, as described in the Arny et al U.S. Pat. Nos. 4,045,910 and 4,161,084, incorporated herein by reference, is to apply to the plants competitive non-ice-nucleating bacteria in an amount sufficient to increase the proportion of non-ice-nucleating bacteria to ice-nucleating bacteria from that normally present on the plants, thereby reducing the probability that sufficient numbers of ice-nucleating bacteria will be able to grow on the plant leaves. This approach requires application of the competitive bacteria at a rather substantial time prior to the onset of freezing temperature and/or at a rather early stage of plant growth so as to enable the competitive bacteria to adequately establish themselves on the plant leaves in order to be effective. Moreover, this approach has not been found to be fully reliable or confidently repeatable in field trails, presumably due to an ability on the part of the ice-nucleating bacteria to re-establish their original proportion to the non-ice-nucleating bacteria on the plants.

SUMMARY OF THE INVENTION

It is, accordingly, a primary object of the present invention to provide an improved method for protecting plants against frost injury by inhibiting ice formation in the plant tissues at moderate supercooling temperatures.

Another object of the invention is to provide an improved method for protecting plants against frost injury in accordance with the preceding object, which is more reliable, convenient and economical than the prior art frost protection procedures.

A further object of the invention is to provide an improved method for protecting plants against frost injury in accordance with the preceding objects, which is ecologically sound and leaves no harmful residue which collects in the environment, and which is harmless to plants and animals.

Still another object of the invention is to provide an improved method for protecting plants against frost injury in accordance with the preceding objects, which can suitably be employed at any stage of plant growth and either relatively shortly prior to the onset of freezing temperature or as a long-term prophylactic treatment at the beginning of a growing season.

A still further object of the invention is to provide an ice nucleation-inhibiting composition for topical application to plants which specifically inhibits the ice-nucleating activity of ice-nucleating bacteria normally present on plants without harming any other living organism, and which is ecologically sound and leaves no harmful residue which collects in the environment.

Yet another object of the invention is to provide an ice nucleation-inhibiting composition in accordance with the preceding object, which is suitable for being conveniently and economically sprayed onto plants by means of conventional irrigation sprinklers or insecticide foggers.

The above and other objects are achieved in accordance with the present invention by means of non-phytotoxic virulent bacteriophages which are species-specific to the ice-nucleating bacteria normally present on plants. When topically applied to frost-sensitive plants, at a time sufficiently prior to the onset of freezing temperature and in a sufficient concentration, such bacteriophages protect the plants against frost injury by inhibiting the ice-nucleating activity of the ice-nucleating bacteria, thereby reducing the temperature at which frost injury occurs to temperatures approaching $-6°$ C. Due to their species specificity, the bacteriophages selectively attack only the ice-nucleating bacteria, and are harmless to any other living organism. They are derived from the natural ecosystem to which they are being applied, and hence their application to plants is ecologically sound and leaves no harmful residue which collects in the environment.

The bacteriophages in accordance with the present invention, along with a suitable non-phytotoxic carrier, may conveniently and economically be sprayed onto the plants by means of conventional irrigation sprinklers or insecticide foggers. Application may suitably be carried out at any stage of plant growth, as late as 24 hours prior to the onset of freezing temperature, or at the beginning of a growing season as a long-term prophylactic treatment. After initial application, the population of the bacteriophages will grow to the limits of its host population or until other natural factors limit such growth.

DESCRIPTION OF PREFERRED EMBODIMENTS

The ice nucleation-inhibiting bacteriophages in accordance with the present invention, are derivable from various local plant material sources, such as grass clippings or other leaf debris, and may be isolated from these sources by viral enrichment procedures employing isolates of any of the various host species of ice-nucleating bacteria, e.g., *Erwinia herbicola* or *Pseudomonus syringae*. Such bacterial isolates are readily obtainable from various culture collections throughout the country, or may be derived from various plants by the well known dilution plating technique.

In the general procedure for isolating the ice nucleation-inhibiting bacteriophages for use in the present invention, the plant material used as the phage source is incubated with a high concentration (e.g., about $10^9$–$10^{10}$ cells per gram of plant material) of the host ice-nucleating bacterial isolate, so that the bacteriophages specific to the host species will have enhanced and preferential growth. After a suitable incubation period, e.g., overnight, the incubation mixture is clarified by centrifugation, and chloroform is then added to the supernatant broth solution so as to kill all the bacterial species therein. Samples of the resulting solution, containing a mixture of bacteriophages, are then plated on a high concentration (e.g., about $10^8$–$10^9$/ml) of the host ice-nucleating bacterial isolate, using the standard agar overlay method, resulting in plaques being formed by the bacteriophages of interest. These plaques are then picked with sterile toothpicks, put in a sterile broth and again replated, and single plaques picked.

The thus isolated bacteriophage is then purified from the plaque by standard differential centrifugation procedures. The bacteriophage is first extracted from the plaque with a suitable buffer, e.g., 0.002 M phosphate buffer, pH 7.0, containing 0.001 M $MgSO_4$ and saturated with chloroform to kill all bacterial species. After removing bacterial debris from the extract, e.g., by centrifugation at $3,000 \times g$ for 10 minutes, the bacteriophage is sedimented at higher centrifugation conditions, e.g., $15,000 \times g$ for one hour.

The resulting isolated and purified bacteriophage is suitably stored in sealed ampules at $4°$ C. in a suitable buffer, e.g., $10^{-3}$ M phosphate buffer, pH 7.0, containing chloroform or 0.1 percent sodium azide to prevent bacterial contamination.

A virulent bacteriophage strain, designated as Bacteriophage Erh 1, which is species-specific to *Erwinia herbicola*, and which has been found to be particularly suitable for use in accordance with the present invention, has been deposited with the American Type Culture Collection, 12301 Parklawn Drive, Rockville, Md. 20852, and is identified by the number ATCC 8366-B. This bacteriophage was isolated and purified in accordance with the general procedure described above, employing fresh grass clippings as the plant material source, and *Erwinia herbicola* subspecies herbicola (ATCC 8366, available from the American Type Culture Collection) as the host ice-nucleating bacterial isolate.

Bacteriophage Erh 1 has been found to have a rather unique morphology, having an elongated rod-like head and a short tail structure with a hollow tail tube, base plate and tail fibers. One major protein and five minor proteins have been identified as phage components. The head structure is transparent, flexible, and can be twisted or flattened by various treatments. The genome of the phage is estimated as having a molecular size of about $21 \times 10^6$ daltons, equivalent to $31 \times 10^3$ base pairs. The bacteriophage may suitably be propogated at $23°$ C. either in broth or agar overlay in a medium containing 5 grams tryptone, 2 grams yeast extract, and 25 grams glycerol per liter of water. While the bacteriophage is stable at temperatures as high as $28°$ C., it is labile at higher temperatures, losing 20 percent of its activity in 30 minutes at $37°$ C., and 90 percent of its activity in 30 minutes at $44°$ C.

The relative efficacy of any given bacteriophage strain, isolated and purified in accordance with the procedure described above, in inhibiting the ice-nucleating activity of its host species of ice-nucleating bacteria, can be readily measured by means of the freezing drop method described by Vali (J. Atmos. Sci., Volume 28, pages 402–409, 1971). This testing procedure is carried out by drawing portions of the sample for testing into a sterile plastic syringe capped with a sterile needle and using the syringe and needle combination to make equal-sized drops on a thermally controlled cold stage. The drops are positioned on a thin square of mylar or aluminum foil held on a cold surface with a light coating of mineral oil. Prior to the application of drops, the foil is coated with silicone resin using paper tissue, to assure that ice nucleation events are not influenced by extraneous nuclei on the foil surface. The silicone also causes drops to "bead up" forming hemispheres. Twenty to 100 drops of 0.01 $cm^3$ are used for each test. The temperature of the sample is then gradually supercooled, and the freezing of the drops is detected visually based on changes of the drops from clear to opaque upon freezing. From the observed freezing temperatures of the drops, ice nucleus activity spectra can be constructed. By comparing the freezing spectrum of a culture of the host species of ice-nucleating bacteria treated with the bacteriophage, with the freezing spectrum of the untreated culture, a good measure of the ice nucleation-inhibiting efficacy of the bacteriophage is obtained.

By following the general isolation, purification, and efficacy testing procedures described herein, and varying the plant material source and/or the host ice-nucleating bacteria species or isolate, it will be readily apparent that an infinite number of non-phytotoxic virulent bacteriophage strains can readily be obtained, and their relative efficacies in the practice of the present invention readily ascertained. It will be understood that any and all of such bacteriophage strains having the ability to inhibit the ice-nucleating activity of ice-nucleating bacteria, are contemplated as being within the scope of the present invention, and that any specific description herein relative to Bacteriophage Erh 1 is given for illustrative purposes only, and is not to be considered in any way limiting.

For use in the practice of the present invention, the ice nucleation-inhibiting bacteriophages, preferably in a senescent state, are most advantageously employed in admixture with a non-phytotoxic carrier therefor. Particularly suitable ice nucleation-inhibiting compositions in accordance with the present invention, are suspensions of the bacteriophages in an aqueous medium, preferably buffered, e.g., with phosphate salts, to a pH within the range of from about 6.5 to about 7.5. Such aqueous medium may suitably contain one or more additives, such as nutrients or protective agents for the bacteriophages. The incorporation into the aqueous medium of gelatin, in a concentration of about 0.1 percent by weight, has been found to be most advantageous in protecting the bacteriophages against surface tension denaturation.

The concentration of bacteriophage in the ice nucleation-inhibiting compositions in accordance with the present invention, will generally be at least about $10^9$ phage particles per ml. Preferably, such bacteriophage concentration will be within the range of from about $5 \times 10^{10}$ to about $2 \times 10^{13}$ phage particles per ml, which represents a concentration of the bacteriophage by a factor of up to about $10^8$ greater than normally found in nature. The optimal concentration of bacteriophage in the composition will be based upon the population of ice-nucleating bacteria present on the plants to be protected, and could be readily determined by bacterial count tests.

The ice nucleation-inhibiting compositions of the present invention may suitable be topically applied to the plants by spraying, for example, by means of conventional irrigation sprinklers, insecticide foggers, or small hand sprayers. The composition should be sprayed on the plants in an amount sufficient to wet the plant leaves, typically in an amount of up to about 0.1 ml per $cm^2$ of leaf surface. For a typical leaf, assuming good wetting, and a concentration of ice-nucleating bacteria of $10^6$ cells per $cm^2$ of leaf surface, for optimum frost protection, the application should be in an amount of at least about $10^{10}$ phage particles per $cm^2$ of leaf surface. This figure would have to be adjusted for higher or lower bacterial counts. Concentrations greater than indicated by bacterial counts can be used, but other than providing a safety factor, will generally offer no significant gains in protection.

Satisfactory frost protection can be obtained with the ice nucleation-inhibiting compositions of the present invention, regardless of the stage of plant growth at the time of the application. Given ideal conditions, frost protection could take place in the space of only a few hours following application. More practically, however, application should take place at least about 24 hours prior to the onset of freezing temperature. After initial application, the population of the bacteriophages will grow to the limits of its host population or until other natural factors limit such growth. The fact that the bacteriophages will propogate on the plants enables application to be made at the beginning of a growing season as a long-term prophylactic treatment.

The frost-sensitive plants protectable against frost injury by means of the ice nucleation-inhibiting compositions of the present invention, include a wide variety of high value food crops and ornamental plants, such as, for example, beans, corn, tomatoes, pumpkins, potatoes, soybeans, a full range of citrus fruits, apples, pears, hard nuts, and a full range of cereal crops. Moreover, since the bacteriophage inhibitors of the present invention are harmless to any living organism other than the specific ice-nucleating bacteria on which they are predators, and since these bacteriophages are part of the natural ecosystem they are being applied to, it is ecologically sound to apply them to any and all crops destined for human consumption. Furthermore, these bacteriophages leave no residue that collects in the environment like many pesticides do, nor do they have any known side effects to plants or animals.

While not intending to be bound by or limited to any particular theory of the mechanism of action of the ice nucleation inhibitors of the present invention, it is believed that the bacteriophage selectively attacks and kills its host species of ice-nucleating bacteria by first attaching by its tail to the outside of the cell wall of the bacterium, and then releasing its DNA or RNA gene component from its head down its hollow tail tube and through the bacterial cell wall into the interior of the bacterial cell. The gene component then replicates the original bacteriophage inside the bacterial cell. During such replication, the ice-nucleation sites present on the bacterial cell wall become deactivated or blocked from inside the cell wall. Continued replication of phage particles within the cell kills the bacterium by causing it to burst, thereby releasing a manyfold increased number of bacteriophages. At this point the bacteriophages go on to infect more bacteria in ever increasing numbers, until they have infected all the ice-nucleating bacteria available to them. In so affecting the ice-nucleating bacteria, they reduce their potential for acting as ice nuclei.

The ice nucleation-inhibiting compositions of the present invention may suitably be applied to plants in conjunction with other known frost prevention compositions to maximize the benefits and advantages of each technique. For example, the competitive non-ice-nucleating bacteria technique described in the Arny, et at., U.S. Pat. Nos. 4,045,910 and 4,161,084, incorporated herein by reference, has not generally been found to be fully reliable or confidently repeatable in field trials, presumably due to an ability on the part of the ice-nucleating bacteria to re-establish their original proportion to the non-ice-nucleating bacteria on the plants.

The species specificity of the ice nucleation-inhibiting bacteriophages of the present invention to ice-nucleating bacteria, would enable them to compatibly be used in conjunction with the Arny, et al., technique, such as, for example, by including non-ice-nucleating bacteria suspended together with the bacteriophages in the same composition in an amount sufficient, when applied to the plants, to increase the proportion of non-ice-nucleating bacteria to ice-nucleating bacteria from that normally present on the plants. The combined effect of such composition would be to kill off the ice-nucleating bacteria on the plants and simultaneously replace them with non-ice-nucleating bacteria, thereby substantially decreasing the probability of the ice-nucleating bacteria re-establishing their original proportion to the non-ice-nucleating bacteria on the plants.

The invention is further illustrated by way of the following examples.

EXAMPLE 1

Employing fresh grass clippings as the source material, and *Erwinia herbicola* subspecies herbicola (ATCC 8366) maintained on 1.2 agar slants containing 5 grams tryptone, 2 grams yeast extract and 25 grams glycerol per liter of water, as the host species of ice-nucleating bacteria, Bacteriophage Erh 1 (ATCC 8366-B) was isolated and purified by means of the following procedure.

Twenty-five ml of fresh broth culture of the host bacterial species, at a concentration of about $2 \times 10^8$/ml was added to 1-2 grams of the fresh grass clippings. The innoculated cultures were shaken over night at 23° C. and clarified by centrifugation at $2,000 \times g$. Chloroform was added to the supernatant broth solution, which was stored in the cold. Various samples of this solution were then plated on the host bacterial species using the standard agar overlay method on the triptone, yeast extract, glycerol medium using 1.2 percent agar in the base layer and 0.5 percent agar in the top layer. 0.1 ml of one-day-old room temperature culture of the host bacterial species, washed off fresh slants and diluted to $2 \times 10^8$/ml, was used to innoculate the soft outer layer. Eight different types of plaques were picked with sterile toothpicks, put in a sterile broth and again replated, and single plaques picked. A variety of phage plaque types were observed, and electron micrographs of the particles obtained. The most common type of plaque was small and clear, but turbid plaques were also observed. Many of the phage particles looked like T1 or λ from the *E. Coli* system with long thin tails and with heads which typically were 7-8 nm wide. One particular phage isolated had a very different type of morphology with a long rod-like head and a short complex tail with a base plate. This phage (Bacteriophage Erh 1) was selected for further purification. The bacteriophage was extracted from the plaque with 0.002 M phosphate buffer, pH 7.0, containing 0.001 M $MgSo_4$ and saturated with chloroform. Bacterial debris was removed by centrifugation at $3,000 \times g$ for 10 minutes, and the bacteriophage was readily sedimented in one hour at $15,000 \times g$ in the angle centrifuge. Concentrated suspensions of the phage could be readily filtered through 0.6 μ Nucleopore filters (95% yield) but passed poorly (8% yield) through 0.47 μ Millipore filters. The phage particles were stored in $10^{-3}$ M phosphate buffer, pH 7.0, and were unaffected by the addition of chloroform or 0.01 percent sodium azide to prevent bacterial contamination.

EXAMPLE 2

The ice nucleation-inhibiting properties of the purified Bacteriophage Erh 1 prepared in accordance with Example 1, when added to a culture of its host species of ice-nucleating bacteria, were determined by means of the freezing drop method described in detail above. At 40 minutes after introduction of the bacteriophage to the bacteria culture, the bacteriophage began to inhibit the ability of the bacteria to induce ice. At 120 minutes after bacteriophage introduction, an ice nucleation inhibition of $-3.5°$ C. was observed. At 100 minutes after bacteriophage introduction, the ice-nucleating bacteria were killed by bursting open to release additional phage that had grown inside them. These new releases of phage go on to infect more of the ice-nucleating bacteria, until all available hosts are infected and so deactivated. In just two hours time, the bacteriophage was able to reduce a healthy population of ice-nucleating bacteria by 90%.

EXAMPLE 3

The ability of Bacteriophage Erh 1, purified in accordance with Example 1, to control frost damage on living plants was tested by the following procedure.

Corn plants (*Zea mays*) were grown in plastic pots in a greenhouse until the four-leaf stage. The pots were randomly divided into treatment groups of up to 100 plants (400 leaves) per test. The plants in some pots were sprayed with solutions of Erwinia herbicola in phosphate buffer, others with buffer alone, and some with Bacteriophage Erh 1. These treatments all served as controls. The test treatment plants were sprayed to wetting with solutions of Erwinia herbicola in concentrations of $10^8$ bacteria cells per ml of solution (concentrations greater than found in nature), then allowed to stabilize for 24 hours prior to addition of Bacteriophage Erh 1 at a concentration of $10^9$ phage particles per ml of liquid. These plants were allowed to stabilize prior to being exposed to a freezing stress of $-5°$ C. along with the control plants.

Frost damage to the plants was quantified 24 hours after removal of the plants from the cold chamber. Frost damage was expressed as the fraction of the leaves per plant which exhibited frost injury as determined by flaccid, discolored leaves. A single area or spot of frost on a leaf classified that leaf as being frost damaged.

The results from these experiments showed that the plants treated with Erwinia herbicola alone sustained greater than 95% frost damage, whereas the buffer and bacteriophage controls exhibited no statistically significant frost damage. The plants treated first with *Erwinia herbicola*, and then Bacteriophage Erh 1, sustained 20-25% less damage than the plants treated with *Erwinia herbicola* alone.

Since the populations of ice-forming *Erwinia herbicola* bacteria on the test plants were substantially higher than those normally observed in nature, and the concentration of Bacteriophage Erh 1 was substantially lower than can be easily obtained in a treatment, it is believed likely that a 40-50% reduction in frost damage would be obtainable under less severe test conditions.

We claim:

1. A method for protecting frost-sensitive plants against frost injury comprising applying to the plants non-phytotoxic virulent bacteriophages which are species-specific to the ice-nucleating bacteria normally present on the plant, said application being at a time sufficiently prior to the onset of freezing temperature and in a sufficient concentration so as to inhibit the ice-nucleating activity of said bacteria, thereby reducing the temperature at which frost injury occurs.

2. The method of claim 1, wherein said bacteriophages comprise phages which are species-specific to *Erwinia herbicola*.

3. The method of claim 2, wherein said *Erwinia herbicola*-specific phages are Bacteriophage Erh 1.

4. The method of claim 1, wherein said bacteriophages are applied to the plants in an aqueous suspension and in an amount sufficient to wet the plant leaves.

5. The method of claim 4, wherein said bacteriophages are applied to the plants by spraying.

6. The method of claim 4, wherein said aqueous suspension contains said bacteriophages in a concentration of at least about $10^9$ phage particles per ml of suspension.

7. The method of claim 6, wherein said bacteriophage concentration is within the range of from about $5 \times 10^{10}$ to about $2 \times 10^{15}$ phage particles per ml of suspension.

8. The method of claim 4, wherein said aqueous suspension is buffered to a pH within the range of from about 6.5 to about 7.5, and contains one or more additives selected from the group consisting of nutrients and protective agents for said bacteriophages.

9. The method of claim 8, wherein said aqueous suspension contains gelatin in a concentration sufficient to protect said bacteriophages against surface tension denaturation.

10. The method of claim 4, wherein said aqueous suspension is applied to the plants in an amount of up to about 0.1 ml per $cm^2$ of leaf surface.

11. The method of claim 1, wherein said bacteriophages are applied to the plants in a senescent state.

12. The method of claim 1, wherein said bacteriophages are applied to the plants in an amount of at least about $10^{10}$ phage particles per $cm^2$ of leaf surface.

13. The method of claim 1, wherein said bacteriophages are applied to the plants at least 24 hours prior to the onset of freezing temperature.

14. The method of claim 1, wherein said bacteriophages are applied to the plants in combination with non-ice-nucleating bacteria in an amount sufficient to increase the proportion of the non-ice nucleating bacteria to ice-nucleating bacteria from that normally present on the plants.

* * * * *

UNITED STATES PATENT AND TRADEMARK OFFICE
CERTIFICATE OF CORRECTION

PATENT NO. : 4,375,734

DATED : March 8, 1983

INVENTOR(S) : Lloyd M. Kozloff et al.

It is certified that error appears in the above-identified patent and that said Letters Patent is hereby corrected as shown below:

Column 2, line 33, "trails" should read -- trials --.

Column 5, line 56, "suitable" should read -- suitably --.

Column 6, line 63, "at." should read -- al. --.

Signed and Sealed this

Twentieth Day of September 1983

[SEAL]

Attest:

Attesting Officer

GERALD J. MOSSINGHOFF

Commissioner of Patents and Trademarks

UNITED STATES PATENT AND TRADEMARK OFFICE
CERTIFICATE OF CORRECTION

PATENT NO. : 4,375,734

DATED : March 8, 1983

INVENTOR(S) : Lloyd M. Kozloff, et al.

It is certified that error appears in the above—identified patent and that said Letters Patent is hereby corrected as shown below:

Column 4, lines 28 - 30: "Erwinia herbicola subspecies herbicola (ATCC 8366, available from the American Type Culture Collection)," should read -- Erwinia herbicola subspecies ananas (ATCC 8366, available from the American Type Culture Collection), --.

Column 7, lines 22 - 23: "Erwinia herbicola subspecies herbicola (ATCC 8366)" should read -- Erwinia herbicola subspecies ananas (ATCC 8366) --.

*Signed and Sealed this*

*Twenty-ninth* Day of *November 1983*

[SEAL]

Attest:

GERALD J. MOSSINGHOFF

*Attesting Officer*   *Commissioner of Patents and Trademarks*